United States Patent [19]

Gesing et al.

[11] Patent Number: 5,223,502
[45] Date of Patent: Jun. 29, 1993

[54] INSECTICIDAL 1,2,3,4-TETRAHYDRO-5-NITROPYR-ROLOPYRIMIDINE DERIVATIVES

[75] Inventors: Ernst R. Gesing, Erkrath-Hochdahl, Fed. Rep. of Germany; Benedikt Becker, Pineta de Laives, Italy; Jürgen Hartwig, Leverkusen; Wilhelm Stendel, Wuppertal, both of Fed. Rep. of Germany

[73] Assignee: Bayer Aktiengesellschaft, Leverkusen, Fed. Rep. of Germany

[21] Appl. No.: 870,196

[22] Filed: Apr. 13, 1992

Related U.S. Application Data

[63] Continuation of Ser. No. 580,249, Sep. 10, 1990, abandoned.

[30] Foreign Application Priority Data

Sep. 27, 1989 [DE] Fed. Rep. of Germany ....... 3932167

[51] Int. Cl.$^5$ .................... A01N 43/54; C07D 471/04
[52] U.S. Cl. .................... 514/258; 514/212; 514/218; 514/241; 514/242; 514/254; 540/544; 540/552; 540/600; 544/180; 544/182; 544/238; 544/279; 544/281
[58] Field of Search .................... 544/281; 514/258

[56] References Cited

U.S. PATENT DOCUMENTS

| | | | |
|---|---|---|---|
| 4,831,036 | 5/1989 | Wolf et al. | 514/258 |
| 4,895,850 | 1/1990 | Gesing et al. | 514/258 |

FOREIGN PATENT DOCUMENTS

| | | |
|---|---|---|
| 0160408 | 6/1985 | European Pat. Off. |
| 0247477 | 2/1987 | European Pat. Off. |
| 0316843 | 5/1989 | European Pat. Off. |
| 0316845 | 5/1989 | European Pat. Off. |
| 3638121 | 3/1987 | Fed. Rep. of Germany |

OTHER PUBLICATIONS

"Trifluromethyl Group in Medicinal Chemistry" by H. L. Yale Journal of Medicinal and Pharmaceutical Chemistry vol. 1, 1969, pp. 121–133.
European Search Report.

*Primary Examiner*—Thurman K. Page
*Assistant Examiner*—Jyothsna Venkat
*Attorney, Agent, or Firm*—Sprung Horn Kramer & Woods

[57] ABSTRACT

Insecticidal 1,2,3,4-Tetrahydro-5-nitropyrimidine derivatives, and salts thereof, of the formula

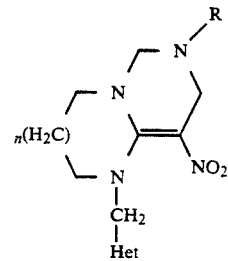

6 Claims, No Drawings

INSECTICIDAL 1,2,3,4-TETRAHYDRO-5-NITROPYRROLOPYRIMIDINE DERIVATIVES

This application is a continuation, of application Ser. No. 580,249, filed Sep. 10, 1990, now abandoned.

The present invention relates to new 1,2,3,4-tetrahydro-5-nitropyrimidine derivatives, to a process for their preparation and to their use in pest-combating agents, in particular as insecticides. Moreover, the new compounds have a strongly pronounced ectoparasiticidal activity.

It is already known that certain pyrimidinothiazines such as, for example, 7-ethyl-9-nitro-3,4,7,8-tetrahydro-(2H, 6H)-pyrimidino-[4,3-b]-1,3-thiazine have insecticidal properties (compare U.S. Pat. No. 4,031,087).

It is furthermore known that certain nitrated nitrogen heterocycles have insecticidal properties (compare EP 0,316,845).

The new 1,2,3,4-tetrahydro-5-nitropyrimidine derivatives of the formula (I)

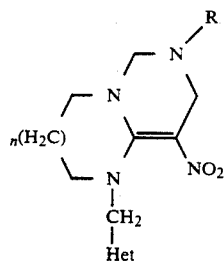

in which n represents the number 0 or 1,

Het represents optionally substituted pyridyl or optionally substituted thiazolyl and R represents monohalogeno-tert-butyl, unsubstituted cycloalkyl having 9 to 18 carbon atoms, cycloalkyl having 7 to 18 carbon atoms to which 1 or 2 carbocycles are fused, monosubstituted or polysubstituted cyclohexyl which is substituted by: alkoxy, mono- or dialkylamino, cycloalkylamino, mono- or dialkylaminocarbonyl, cycloalkyl, cycloalkylalkyl and/or by phenylalkyl, cyclohexyl to which 1 or 2 other carbocycles are fused, cycloalkylalkyl having 3 to 10 carbon atoms in the cycloalkyl and 1 to 5 carbon atoms in the alkyl moiety, which is monosubstituted or polysubstituted in the cycloalkyl moiety, heterocyclyl having 2 to 8 carbon atoms and 1 to 4 heteroatoms (preferably nitrogen, oxygen and/or sulphur) or heterogroupings (preferably $SO_2$) which is optionally monosubstituted or polysubstituted and to which 1 or 2 carbocycles are optionally fused, tetrahydrofurylalkyl having 1 to 6 carbon atoms in the alkyl moiety and which is optionally monosubstituted or polysubstituted or piperidylalkyl having 1 to 6 carbon atoms in the alkyl moiety which is optionally monosubstituted or polysubstituted, adamantyl, adamantylmethyl or one of the following groupings (A), (B) and (C), which are optionally substituted:

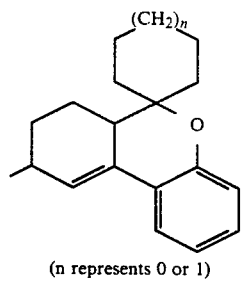

(n represents 0 or 1)

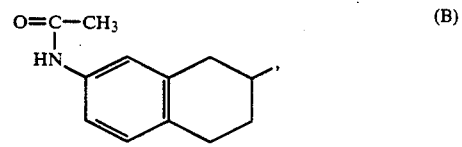

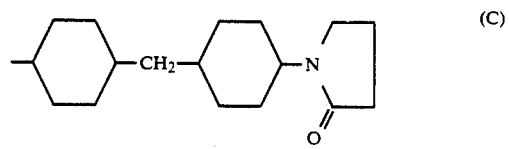

and their acid addition salts have now been found.

Some of the new 1,2,3,4-tetrahydro-5-nitro pyrimidine derivatives of the formula (I) have an asymmetrically substituted carbon atom and can therefore be obtained in the two optical isomer forms. The invention relates both to the isomer mixtures and to the individual isomers.

It has furthermore been found that the 1,2,3,4-tetrahydro-5-nitropyrimidine derivatives of the formula (I) and their acid addition salts are obtained when nitromethylene derivatives of the formula (II)

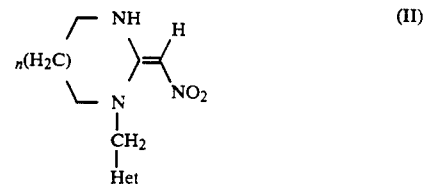

in which n and Het have the abovementioned meanings, are reacted with amines of the formula (III)

in which

R has the abovementioned meaning, in the presence of at least a two-fold molar amount of formaldehyde, if appropriate in the presence of acidic catalysts and if appropriate in the presence of diluents and, if appropriate, acids are adducted to the compounds obtained.

Monohalogeno-tert-butyl in the definition of R preferably means fluoro- chloro- or bromo-, in particular fluoro-tert-butyl.

Carbocycles which can be fused to other rings are saturated or unsaturated or aromatic. They preferably form, with the carbon atoms to which they are fused, cyclohexyl or phenyl rings. The carbocycles may carry one or more identical or different substituents from those mentioned further below. However, they are preferably unsubstituted.

Heterocyclyl in the definition of R preferably means in the general formulae heteroparaffinic, heteroaromatic and heteroolefinic 5- to 7-membered rings preferably having 1 to 3, in particular 1 or 2 identical or different heteroatoms or heterogroups. Heteroatoms are oxygen, sulphur or nitrogen and heterogroups are $SO_2$ or N-($C_1$-$C_4$-alkyl). Pyrrolidinyl, piperidinyl, furyl, thiophenyl, pyrazolyl, imidazolyl, 1,2,3- and 1,2,4-triazolyl, oxazolyl, isoxazolyl, thiazolyl, isothiazolyl, 1,2,3-, 1,3,4-, 1,2,4- and 1,2,5-oxadiazolyl, azepinyl, pyrrolyl, isopyrrolyl, pyridyl, piperazinyl, pyridazinyl, pyrimidinyl, pyrazinyl, 1,3,5-, 1,2,4- and 1,2,3-triazinyl, 1,2,4-, 1,3,2-, 1,3,6- and 1,2,6-oxazinyl, oxepinyl, thiepinyl and 1,2,4-diazepinyl may preferably be mentioned.

The optionally substituted radicals in the general formulae can carry one or more, preferably 1 to 3, in particular 1 or 2 identical or different substituents. Substituents which may preferably be mentioned are: alkyl preferably having 1 to 4, in particular 1 or 2 carbon atoms, such as methyl, ethyl, n- and i-propyl and n-, i- and t-butyl; cycloalkyl, cycloalkylamino or cycloalkylalkyl preferably having 3 to 7, in particular 5 or 6 carbon atoms in the cycloalkyl moiety and preferably 1 to 5, in particular 1 to 4 carbon atoms in the straight-chain or branched alkyl moiety; aralkyl, preferably phenylalkyl preferably having 1 to 4, in particular 1 to 3 carbon atoms in the alkyl moiety; alkoxy preferably having 1 to 4, in particular 1 or 2 carbon atoms, such as methoxy, ethoxy, n- and i-propoxy and n-, i- and t-butoxy, alkylthio preferably having 1 to 4, in particular 1 or 2 carbon atoms, such as methylthio, ethylthio, n- and i-propylthio and n-, i- and t-butylthio; halogenoalkyl preferably having 1 to 4, in particular 1 or 2 carbon atoms and preferably 1 to 5, in particular 1 to 3 halogen atoms, the halogen atoms being identical or different and being, as halogen atoms, preferably fluorine, chlorine or bromine, in particular fluorine, such as trifluoromethyl; hydroxyl; halogen, preferably fluorine, chlorine, bromine and iodine, in particular fluorine, chlorine and bromine; cyano; nitro; amino; monoalkyl- and dialkylamino or mono- and dialkylaminocarbonyl preferably having 1 to 4, in particular 1 or 2 carbon atoms per alkyl group, such as methylamino, methyl-ethyl-amino, n- and i-propyl-amino, and methyl-n-butylamino; carboxyl; carbalkoxy preferably having 2 to 4, in particular 2 or 3 carbon atoms, such as carbomethoxy and carboethoxy; sulpho (—$SO_3H$); alkylsulphonyl preferably having 1 to 4, in particular 1 or 2 carbon atoms, such as methylsulphonyl and ethylsulphonyl; arylsulphonyl preferably having 6 or 10 aryl carbon atoms, such as phenylsulphonyl.

The pyridyl and thiazolyl radicals in the definition of Het preferably carry 1 or 2 identical or different substituents, halogen (fluorine, chlorine, bromine and iodine, preferably fluorine or chlorine, in particular chlorine) preferably being mentioned as substituents. Particularly preferably, Het represents 2-chloro-1,3-thiazol-5-yl and 2-chloropyridin-5-yl.

The preferred definitions mentioned here also apply to the preferred combinations of definitions mentioned in the following in a corresponding manner.

Surprisingly, the 1,2,3,4-tetrahydro-5-nitro pyrimidine derivatives of the formula (I) according to the invention are distinguished in an outstanding manner by a high activity as insecticides and ectoparasiticides.

The invention preferably relates to compounds of the formula (I), in which n represents the numbers 0 or 1, Het represents pyridyl optionally substituted by halogen or thiazolyl optionally substituted by halogen and R represents tert-butyl, monosubstituted by fluorine or chlorine, unsubstituted cycloalkyl having 9 to 16 carbon atoms, cycloalkyl having 7 to 16 carbon atoms, to which 1 or 2 6-membered aromatic or saturated carbocycles are fused, monosubstituted to trisubstituted cyclohexyl which is substituted by: alkoxy having 1 to 4 carbon atoms, mono- or dialkylamino in each case having 1 to 4 carbon atoms in the individual alkyl moieties, cycloalkylamino having 3 to 7 carbon atoms, mono- or dialkylaminocarbonyl in each case having 1 to 4 carbon atoms in the individual alkyl moieties, cycloalkyl having 3 to 7 carbon atoms, cycloalkylalkyl having 3 to 7 carbon atoms in the cycloalkyl and 1 to 5 carbon atoms in the alkyl moiety and/or by phenylalkyl having 1 to 4 carbon atoms in the alkyl moiety, cyclohexyl, to which 1 or 2 6-membered aromatic or saturated carbocycles are fused, cycloalkylalkyl having 3 to 7 carbon atoms in the cycloalkyl and 1 to 4 carbon atoms in the alkyl moiety, which is monosubstituted to trisubstituted in the cycloalkyl moiety by alkyl or halogenoalkyl in each case having 1 to 4 carbon atoms and optionally 1 to 9 fluorine and/or chlorine atoms, heterocyclyl having 3 to 6 carbon atoms and 1 to 3 heteroatoms or heterogroupings from the series comprising oxygen, sulphur, nitrogen and $SO_2$, which is optionally monosubstituted or polysubstituted by alkyl and/or halogenoalkyl in each case having 1 to 4 carbon atoms and optionally 1 to 9 fluorine and/or chlorine atoms and to which 1 or 2 6-membered aromatic or saturated carbocycles are optionally fused, tetrahydrofurylalkyl having 1 to 4 carbon atoms in the alkyl moiety which is optionally monosubstituted to trisubstituted by alkyl and/or halogenoalkyl in each case having 1 to 4 carbon atoms and optionally 1 to 9 fluorine and/or chlorine atoms or piperidylalkyl having 1 to 4 carbon atoms in the alkyl moiety which is optionally monosubstituted to trisubstituted by alkyl and/or halogenoalkyl in each case having 1 to 4 carbon atoms and optionally 1 to 9 fluorine and/or chlorine atoms or one of the following groupings (A) to (F), which are optionally substituted by alkyl having 1 to 4 carbon atoms:

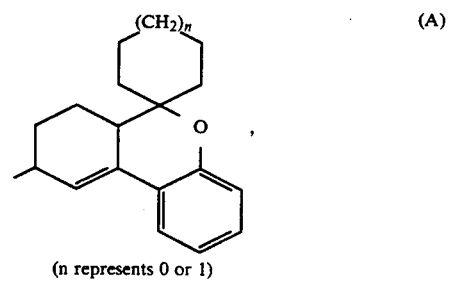

(A)

(n represents 0 or 1)

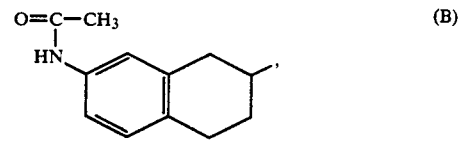

(B)

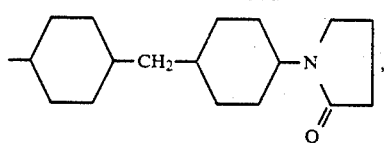 (C)

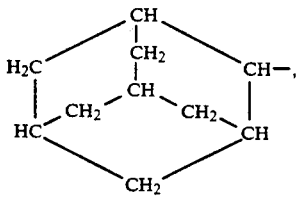 (D)

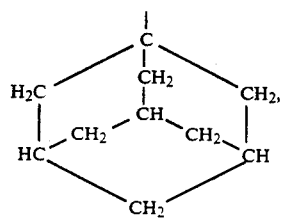 (E)

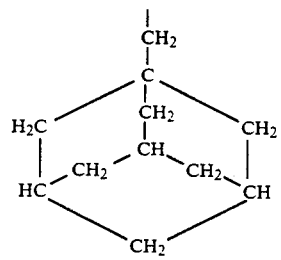 (F)

Particularly preferred compounds of the formula (I) are those in which
n represents the number 0 or 1,
Het represents

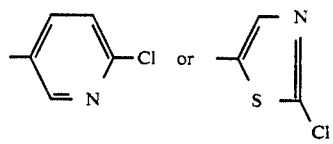

and

R represents fluoro-tert-butyl, unsubstituted cycloalkyl having 9 to 12 carbon atoms, cycloalkyl having 7 to 12 carbon atoms, to which 1 or 2 6-membered aromatic carbocycles are fused, monosubstituted or disubstituted cyclohexyl, which is substituted by: methoxy, ethoxy, n- or i-propoxy, methylamino, dimethylamino, ethylamino, diethylamino, ethylmethylamino, n-propylamino, di-(n-propyl)amino, methyl(n-propyl)amino, ethyl(n-propyl)amino, isopropylamino, di(isopropyl)amino, methylisopropylamino, ethylisopropylamino, isopropyl(n-propyl)amino or cyclopentylamino, cyclohexylamino, methylaminocarbonyl, dimethylaminocarbonyl, ethylaminocarbonyl, diethylaminocarbonyl, ethylmethylaminocarbonyl, n-propylaminocarbonyl, di(n-propyl)aminocarbonyl, methyl(n-propyl)aminocarbonyl, ethyl(n-propyl)aminocarbonyl, isopropylaminocarbonyl, di(isopropyl)aminocarbonyl, methylisopropylaminocarbonyl, ethylisopropylaminocarbonyl, isopropyl(n-propyl)aminocarbonyl, cyclopentyl, cyclohexyl, cyclopentylmethyl, cyclopentylethyl, cyclopentyl-n-propyl, cyclopentylisopropyl, cyclohexylmethyl, cyclohexylethyl, cyclohexyl-n-propyl, cyclohexylisopropyl, phenylmethyl, phenylethyl, phenyl-n-propyl and/or phenylisopropyl, cyclohexyl to which 1 or 2 6-membered aromatic or saturated carbocycles are fused, cyclopentylmethyl, cyclopentylethyl, cyclohexylmethyl or cyclohexylethyl, these radicals being monosubstituted or disubstituted in the cycloalkyl moiety by methyl and/or trifluoromethyl, heterocyclyl having 5 to 12 carbon atoms and 1 or 2 hetero atoms or heterogroupings from the series comprising oxygen, sulphur, nitrogen and $SO_2$, which is optionally monosubstituted to hexasubstituted by methyl and/or trifluoromethyl and to which 1 or 2 6-membered aromatic carbocycles are optionally fused, tetrahydrofurylmethyl or tetrahydrofurylethyl, piperidylmethyl, piperidylethyl or piperidyl-n-propyl or one of the following groupings (A) to (F):

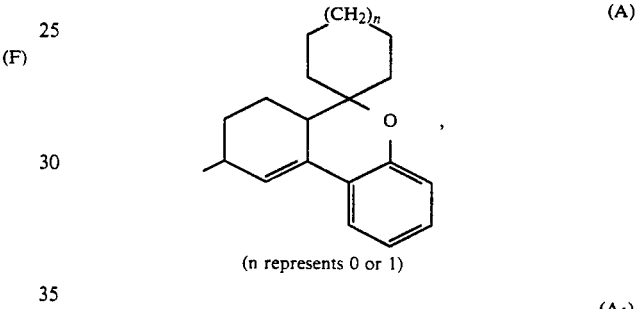 (A)

(n represents 0 or 1)

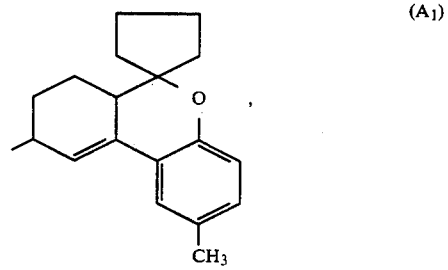 ($A_1$)

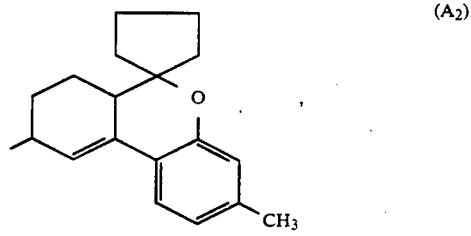 ($A_2$)

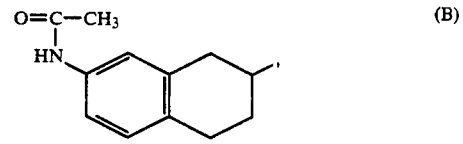 (B)

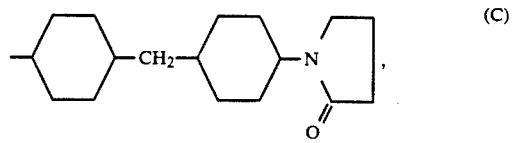 (C)

-continued

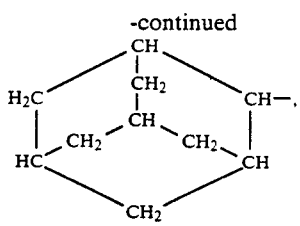

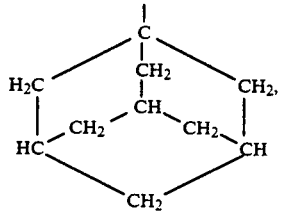

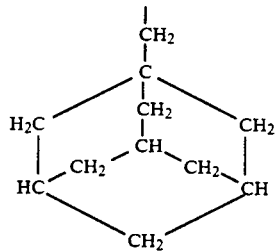

The general and preferred radical definitions indicated for the compound of the general formula (I) also apply correspondingly to the compounds of the other general formulae (intermediates or precursors).

Preferred compounds according to the invention are also addition products of acids and the 1,2,3,4-tetrahydro-5-nitropyrimidine derivatives of the formula (I).

The acids which can be adducted preferably include hydrohalic acids, such as, for example, hydrochloric acid and hydrobromic acid, in particular hydrochloric acid, and in addition phosphoric acid, sulphuric acid, nitric acid, acetic acid, oxalic acid, malonic acid, succinic acid, malic acid, tartaric acid, maleic acid, fumaric acid, methanesulphonic acid, benzoic acid, substituted benzoic acids, formic acid, chloroacetic acid, toluenesulphonic acid, benzenesulphonic acid, trichloroacetic acid, phthalic acid, naphthalenesulphonic acid, nicotinic acid, citric acid and ascorbic acid.

If, for example, 3-(2-chloro-pyridin-5-yl-methyl)-2-nitromethylene-imidazolidine, 4-(1-methyl-1-cyclohexylethyl)cyclohexylamine and at least a two-fold molar amount of formaldehyde are used as starting materials for the process according to the invention, the corresponding reaction can be represented by the following equation:

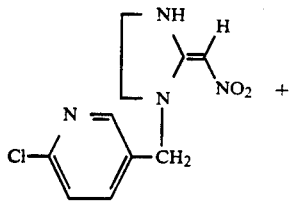

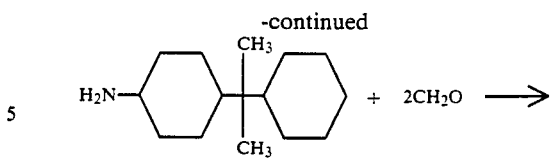

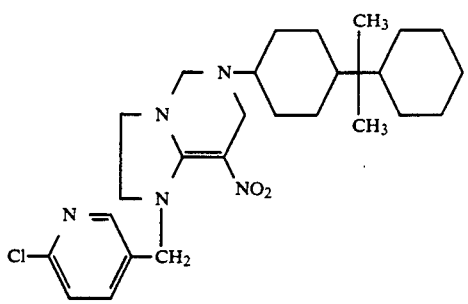

The compounds of the formula (II) to be used as starting materials in the process according to the invention are known and/or can be prepared by known methods (compare, for example, DE-OS (German Published Specification) 2,514,402, EP-OS (European Published Specification) 136,636 (which is equivalent to U.S. Pat. No. 4,90,272, EP-OS 154,178 (which is equivalent to U.S. Pat. No. 4,647,570 and EP-OS 163,855 (which is equivalent to U.S. Pat. No. 4,678,795)).

The amines of the formula (III) additionally to be used as starting materials in the process according to the invention are generally known compounds of organic chemistry.

The process according to the invention for the preparation of the new compounds of the formula (I) is preferably carried out using diluents. Suitable diluents in this case are water and organic solvents which are inert to the reaction. These preferably include aliphatic and aromatic, optionally halogenated hydrocarbons such as pentane, hexane, heptane, cyclohexane, petroleum ether, benzine, ligroin, benzene, toluene, xylene, methylene chloride, ethylene chloride, chloroform, carbon tetrachloride, chlorobenzene and o-dichlorobenzene, ethers such as diethyl ether and dibutyl ether, glycol dimethyl ether and diglycol dimethyl ether, tetrahydrofuran and dioxane, and alcohols, such as methanol, ethanol, n-propanol and isopropanol. Mixtures of alcohols and water are preferably employed.

The process according to the invention is optionally carried out in the presence of acidic, non-oxidizing catalysts. Those which have proved particularly suitable are hydrohalic acids such as hydrochloric acid and hydrobromic acid, phosphoric acid, and lower carboxylic acids such as acetic acid and propionic acid.

The reaction temperatures can be varied within a relatively wide range when carrying out the process according to the invention. In general, the reaction is carried out at temperatures between $-20°$ C. and $+120°$ C., preferably at temperatures between $0°$ C. and $+80°$ C.

The process according to the invention is in general carried out under normal pressure. However, it is also possible to work at elevated or reduced pressure.

In order to carry out the process according to the invention, 1 to 1.5 moles, preferably 1 to 1.2 moles of amine of the formula (III) and 2 to 4 moles, preferably 2 to 3 moles of a formaldehyde are employed per mole of nitromethylene derivative of the formula (II).

The amines of the formula (III) can optionally be employed as aqueous solutions. When using gaseous amines of the formula (III), these compounds can be passed through the mixture of diluents, compounds of the formula (II) and formaldehyde. Formaldehyde is employed in aqueous solution for the process according to the invention. The reactions are in general carried out in a suitable diluent and the reaction mixture is stirred for several hours at the temperature necessary in each case. Working up is in each case carried out by customary methods in the process according to the invention.

The acid addition salts of the compounds of the formula (I) can be obtained in a simple manner by customary salt formation methods, for example by dissolving a compound of the formula (I) in a suitable inert solvent and adding the acid, for example hydrochloric acid, and can be isolated in a known manner, for example by filtering off and, if appropriate, can be purified by washing with an inert organic solvent.

The active compounds are suitable for combating animal pests, in particular insects and nematodes, encountered in agriculture, in forestry, in the protection of stored products and of materials, and in the hygiene field, and have good plant tolerance and favourable toxicity to warm-blooded animals. They are active against normally sensitive and resistant species and against all or some stages of development. The abovementioned pests include:

From the order of the Isopoda, for example, *Oniscus asellus*, *Armadillidium vulgare* and *Porcellio scaber*. From the order of the Diplopoda, for example, *Blaniulus guttulatus*. From the order of the Chilopoda, for example, *Geophilus carpophagus* and *Scutigera spec*. From the order of the Symphyla, for example, *Scutigerella immaculata*. From the order of the Thysanura, for example, *Lepisma saccharina*. From the order of the Collembola, for example, *Onychiurus armatus*. From the order of the Orthoptera, for example, *Blatta orientalis*, *Periplaneta americana*, *Leucophaea maderae*, *Blattella germanica*, *Acheta domesticus*, *Gryllotalpa spp.*, *Locusta migratoria migratorioides*, *Melanoplus differentialis* and *Schistocerca gregaria*. From the order of Dermaptera, for example, *Forficula auricularia*. From the order of the Isoptera, for example, *Reticulitermes* spp. From the order of the Anoplura, for example, *Phylloxera vastatrix*, *Pemphigus spp.*, *Pediculus humanus corporis*, *Haematopinus spp.* and *Linognathus spp.* From the order of the Mallophaga, for example, *Trichodectes spp.* and *Damalinea spp.* From the order of the Thysanoptera, for example, *Hercinothrips femoralis* and *Thrips tabaci*. From the order of the Heteroptera, for example, *Eurygaster spp.*, *Dysdercus intermedius*, *Piesma quadrata*, *Cimex lectularius*, *Rhodnius prolixus* and *Triatoma spp.* From the order of the Homoptera, for example, *Aleurodes brassicae*, *Bemisia tabaci*, *Trialeurodes vaporariorum*, *Aphis gossypii*, *Brevicoryne brassicae*, *Cryptomyzus ribis*, *Aphis fabae*, *Doralis pomi*, *Eriosoma lanigerum*, *Hyalopterus arundinis*, *Macrosiphum avenae*, *Myzus spp.*, *Phorodon humuli*, *Rhopalosiphum padi*, *Empoasca spp.*, *Euscelis bilobatus*, *Nephotettix cincticeps*, *Lecanium corni*, *Saissetia oleae*, *Laodelphax striatellus*, *Nilaparvata lugens*, *Aonidiella aurantii*, *Aspidiotus hederae*, *Pseudococcus spp.* and *Psylla spp.* From the order of the Lepidoptera, for example, *Pectinophora gossypiella*, *Bupalus piniarius*, *Cheimatobia brumata*, *Lithocolletis blancardella*, *Hyponomeuta padella*, *Plutella maculipennis*, *Malacosoma neustria*, *Euproctis chrysorrhoea*, *Lymantria spp.* *Bucculatrix thurberiella*, *Phyllocnistis citrella*, *Agrotis spp.*, *Euxoa spp.*, *Feltia spp.*, *Earias insulana*, *Heliothis spp.*, *Spodoptera exigua Mamestra brassicae*, *Panolis flammea*, *Prodenia litura*, *Spodoptera spp.*, *Trichoplusia ni*, *Carpocapsa pomenella*, *Pieris spp.*, *Chilo spp.*, *Pyrausta nubilalis*, *Ephestia kuehniella*, *Galleria mellonella*, *Tineola bisselliella*, *Tinea pellionella*, *Hofmannophila pseudospretella*, *Cacoecia podana*, *capua reticulana*, *Choristoneura fumiferana*, *Clysia ambiguella*, *Homona magnanima* and *Tortrix viridana*.

From the order of the Coleoptera, for example, *Anobium punctatum*, *Rhizopertha dominica*, *Acanthoscelides obtectus*, *Hylotrupes bajulus*, *Agelastica alni*, *Leptinotarsa decemlineata*, *Phaedon cochleariae*, *Diabrotica spp.*, *Psylliodes chrysocephala*, *Epilachna varivestis*, *Atomaria spp.*, *Oryzaephilus surinamensis*, *Anthonomus spp.*, *Sitophilus spp.*, *Otiorrhynchus sulcatus*, *Cosmopolites sordidus*, *Ceuthorrhynchus assimilis*, *Hypera postica*, *Dermestes spp.*, *Trogoderma spp.*, *Anthrenus spp.*, *Attagenus spp.*, *Lyctus spp.*, *Meligethes aeneus*, *Ptinus spp.*, *Niptus hololeucus*, *Gibbium psylloides*, *Tribolium spp.*, *Tenebrio molitor*, *Agriotes spp.*, *Conoderus spp.*, *Melolontha melolontha*, *Amphimallon solstitialis* and *Costelytra zealandica*. From the order of the Hymenoptera, for example, *Diprion spp.*, *Hoplocampa spp.*, *Lasius spp.*, *Monomorium pharaonis* and *Vespa spp.* From the order of the Diptera, for example, *Aedes spp.*, *Anopheles spp.*, *Culex spp.*, *Drosophila melanogaster*, *Musca spp.*, *Fannia spp.*, *Calliphora erythrocephala*, *Lucilia spp.*, *Chrysomyia spp.*, *Cuterebra spp.*, *Gastrophilus spp.*, *Hyppobosca spp.*, *Stomoxys spp.*, *Oestrus spp.*, *Hypoderma spp.*, *Tabanus spp.*, *Tannia spp.*, *Bibio hortulanus*, *Oscinella frit*, *Phorbia spp.*, *Pegomyia hyoscyami*, *Ceratitis capitata*, *pacus oleae* and *Tipula paludosa*.

From the order of the Siphonaptera, for example, *Xenopsylla cheopis* and *Ceratophyllus spp.* From the order of the Arachnida, for example, *Scorpio maurus* and *Latrodectus mactans*.

The active compounds of the formula (I) are distinguished by an outstanding insecticidal activity. They show, in particular when used as leaf insecticides and soil insecticides, an outstanding action against grubs such as, for example, *Phorbia antiqua* grubs, against beetle larvae, such as, for example, *Phaedon cochleariae* and aphids, such as, for example, *Aphis fabae*.

The active compounds of the formula (I) according to the invention furthermore show an outstanding root-systemic action, for example against *Phaedon cochleariae* larvae and aphids such as *Myzus persicae* and are moreover also excellently suitable for the treatment of seed, for example against grubs such as *Phorbia antiqua*, against beetle larvae such as *Phaedon cochleariae* and aphids such as *Aphis fabae*.

The active compounds according to the invention are additionally outstandingly suitable for combating ectoparasites such as, for example, *Lucilia cuprina* larvae, *Blattella germanica* and *Sitophilus granarius*.

The new compounds are thus particularly suitable for use for combating leaf insects and soil insects and also for the treatment of seed and combating ectoparasites. The compounds are particularly preferably employed as plant protection agents.

The active compounds can be converted to the customary formulations, such as solutions, emulsions, suspensions, powders, foams, pastes, granules, aerosols, natural and synthetic materials impregnated with active compound, very fine capsules in polymeric substances and in coating compositions for seed, and formulations used with burning equipment, such as fumigating cartridges, fumigating cans, fumigating coils and the like, as well as ULV cold mist and warm mist formulations.

These formulations are produced in a known manner, for example by mixing the active compounds with extenders, that is, liquid solvents, liquefied gases under pressure, and/or solid carriers, optionally with the use of surface-active agents, that is emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water; by liquefied gaseous extenders or carriers are meant liquids which are gaseous at ambient temperature and under atmospheric pressure, for example aerosol propellants, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly disperse silica, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foamforming agents there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumin hydrolysis products; as dispersing agents there are suitable: for example lignin-sulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

The active compounds according to the invention can be present in their commercially available formulations and in the use forms, prepared from these formulations, as a mixture with other active compounds, such as insecticides, attractants, sterilizing agents, acaricides, nematicides, fungicides, growth-regulating substances or herbicides. The insecticides include, for example, phosphates, carbamates, carboxylates, chlorinated hydrocarbons, phenylureas and substances produced by microorganisms, inter alia.

The active compounds according to the invention can furthermore be present in their commercially available formulations and in the use forms, prepared from these formulations, as a mixture with synergistic agents. Synergistic agents are compounds which increase the action of the active compounds, without it being necessary for the synergistic agent added to be active itself.

The active compound content of the use forms prepared from the commercially available formulations can vary within wide limits. The active compound concentration of the use forms can be from 0.0000001 to 95% by weight of active compound, preferably between 0.0001 to 1% by weight.

The compounds are employed in a customary manner appropriate for the use forms.

When used against hygiene pests and pests of stored products, the active compounds are distinguished by an excellent residual action on wood and clay as well as a good stability to alkali on limed substrates.

The active compounds according to the invention are also suitable for combating insects, midges, ticks etc. in the sectors of animal keeping and cattle breeding; better results, for example higher milk production, greater weight, more attractive animal pelt, etc., can be achieved by combating the pests.

The active compounds show, in particular when used as ectoparasiticides, an excellent action against blowfly larvae such as, for example, Lucilia cuprina.

The application of the active compounds according to the invention occurs in this sector in a known fashion, such as by external application in the form of, for example, dipping, spraying, pouring-on, spotting-on and dusting of the animals or by appropriate treatment of the environment of the animals (for example animal pens).

The preparation and the biological effectiveness of the compounds according to the invention will be explained with reference to the example below (in the Preparation Examples room temperature means: 18° to 20° C.):

PREPARATION EXAMPLES

Example 1

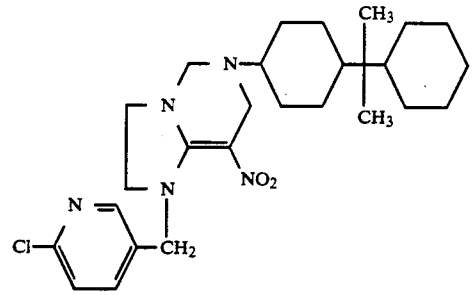

1.5 ml (0.02 mol) of 37% aqueous formaldehyde solution are added dropwise at room temperature to a mixture of 2.54 g (0.01 mol) of 3-(2-chloropyridin-5-yl-methyl)-2-nitromethylene-imidazolidine and 2.23 g (0.01 mol) of 4-(1-methyl-1-cyclohexylethyl)cyclohexylamine in 90 ml of methanol and the mixture is heated under reflux for 3 hours. After cooling to room temperature, the solvent is removed in vacuo, ether is added to the residue and the precipitate is filtered off with suction.

3.5 g (70% of theory) of 6,7-dihydro-6-[4-(1-methyl-1-cyclohexylethyl)-cyclohexyl]-8-nitro-(5H)-3-(2-chloropyridin-5-yl-methyl)-imidazolidino-[2,3-f]-pyrimidine of melting point 115° C. (dec.) are obtained.

The compounds of the formula (I) indicated in Table 1 below can be prepared analogously to Example 1 or other processes according to the invention:

TABLE 1

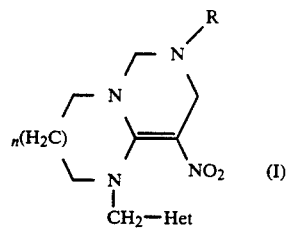

(I)

| Ex. No. | n | R | Het | Melting point |
|---|---|---|---|---|
| 2 | 0 | cyclobutyl | 2-chloropyridin-5-yl | 175–179° C. |
| 3 | 1 | cyclopentyl-CH2-SO2- | 2-chloropyridin-5-yl | oil |
| 4 | 1 | adamantyl | 2-chloropyridin-5-yl | 156° C. |
| 5 | 0 | 1,2,3,4-tetrahydronaphth-1-yl | 2-chloropyridin-5-yl | 164–165° C. |
| 6 | 1 | 1,2,3,4-tetrahydronaphth-1-yl | 2-chloropyridin-5-yl | 172–175° C. |
| 7 | 1 | cyclobutyl | 2-chloropyridin-5-yl | 158–164° C. |
| 8 | 0 | —CH2CH2CH2—N(piperidinyl) | 2-chloropyridin-5-yl | 103–112° C. |

TABLE 1-continued
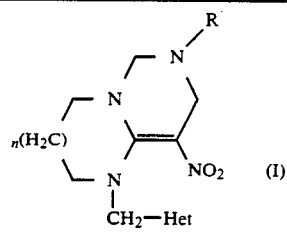
| Ex. No. | n | R | Het | Melting point |
|---|---|---|---|---|
| 9 | 0 | decahydronaphthyl | 2-chloro-5-pyridyl | 144° C. (dec.) |
| 10 | 1 | decahydronaphthyl | 2-chloro-5-pyridyl | 114–120° C. |
| 11 | 0 | decahydronaphthyl | 2-chloro-5-pyridyl | 119–123° C. (dec.) |
| 12 | 1 | decahydronaphthyl | 2-chloro-5-pyridyl | 134° C. (dec.) |
| 13 | 0 | cyclohexyl-$N(C_2H_5)_2$ | 2-chloro-5-pyridyl | 140–148° C. |
| 14 | 1 | cyclohexyl-$N(C_2H_5)_2$ | 2-chloro-5-pyridyl | 148° C. (dec.) |
| 15 | 0 | cyclohexyl-$OC_2H_5$ | 2-chloro-5-pyridyl | 127–134° C. |
| 16 | 1 | cyclohexyl-$OC_2H_5$ | 2-chloro-5-pyridyl | 153° C. (dec.) |

TABLE 1-continued

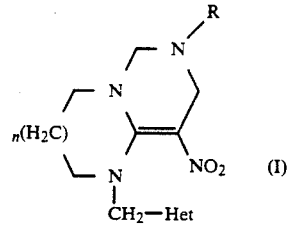

| Ex. No. | n | R | Het | Melting point |
|---|---|---|---|---|
| 17 | 0 | cyclohexyl-NH-cyclohexyl | 2-chloropyridin-5-yl | 146–150° C. |
| 18 | 1 | cyclohexyl-NH-cyclohexyl | 2-chloropyridin-5-yl | 139–141° C. |
| 19 | 0 | cyclohexyl-cyclohexyl | 2-chloropyridin-5-yl | 173° C. (dec.) |
| 20 | 1 | cyclohexyl-cyclohexyl | 2-chloropyridin-5-yl | 159° C. (dec.) |
| 21 | 1 | cyclohexyl-C(CH₃)₂-cyclohexyl | 2-chloropyridin-5-yl | 139–142° C. |
| 22 | 0 | bicyclohexyl | 2-chloropyridin-5-yl | 98° C. |
| 23 | 0 | cyclohexyl-C(CH₃)₂-phenyl | 2-chloropyridin-5-yl | 158° C. |
| 24 | 0 | spiro polycyclic structure | 2-chloropyridin-5-yl | 190° C. (dec.) |

TABLE 1-continued
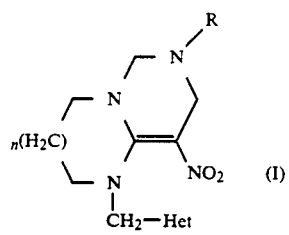
| Ex. No. | n | R | Het | Melting point |
|---|---|---|---|---|
| 25 | 0 | 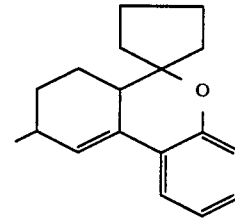 isomer | 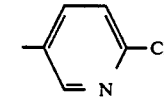 | 91–101° C. (dec.) |
| 26 | 0 | 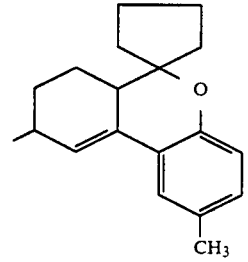 | 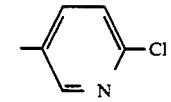 | 111° C. |
| 27 | 0 | 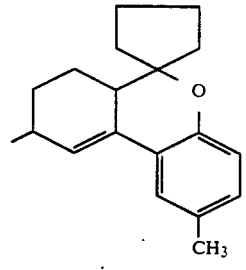 isomer | 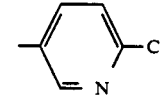 | 145° C. (dec.) |
| 28 | 0 | 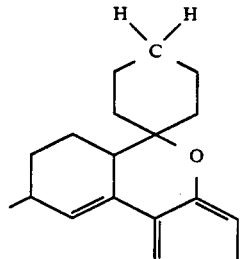 | 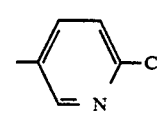 | 130–135° C. (dec.) |

TABLE 1-continued
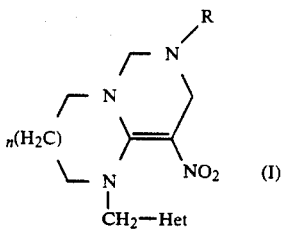  (I)
| Ex. No. | n | R | Het | Melting point |
|---|---|---|---|---|
| 29 | 0 |  isomer | 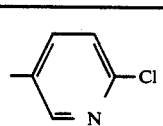 | 179° C. (dec.) |
| 30 | 0 | 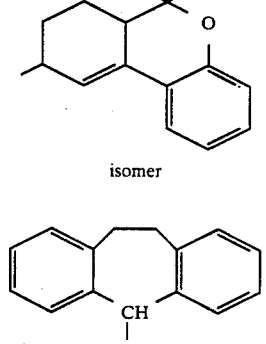 | 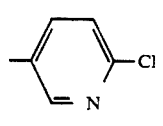 | 160–174° C. (dec.) |
| 31 | 1 | 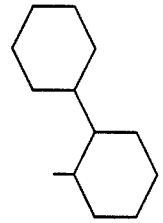 | 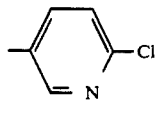 | 72° C. |
| 32 | 1 | 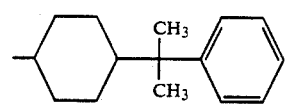 | 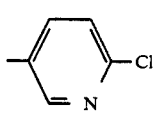 | 165° C. (dec.) |
| 33 | 1 | 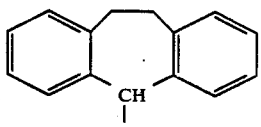 | 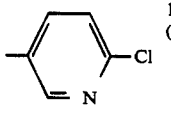 | 168° C. (dec.) |
| 34 | 0 | 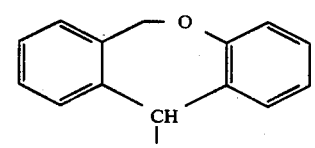 | 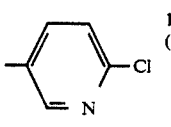 | 168° C. (dec.) |
| 35 | 0 | 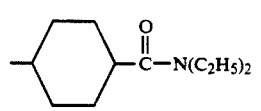 | 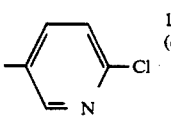 | 122–132° C. (dec.) |

TABLE 1-continued $$\text{structure (I)}$$

| Ex. No. | n | R | Het | Melting point |
|---|---|---|---|---|
| 36 | 1 | (spirocyclopentyl-cyclohexenyl-methylphenyl-O- structure) | 2-chloro-5-pyridyl | 115° C. |
| 37 | 0 | methylcyclohexyl-CH₂-cyclohexyl-N(pyrrolidinone) | 2-chloro-5-pyridyl | 149° C. |
| 38 | 0 | (CH₃)₂C(CH₂F)– | 2-chloro-5-pyridyl | 167° C. |
| 39 | 0 | 3-methyl-tetrahydrothiophene-SO₂ | 2-chloro-5-pyridyl | 87–90° C. (dec.) |
| 40 | 0 | (CH₃)₂C(CH₃)CH₂CH(CH₃)CH₂C(CH₃)₂N–CH₃ | 2-chloro-5-pyridyl | 182° C. (dec.) |
| 41 | 1 | –CH₂CH₂CH₂–N(piperidinyl) | 2-chloro-5-pyridyl | 123–125° C. |
| 42 | 1 | (CH₃)₂C(CH₂F)– | 2-chloro-5-pyridyl | — |
| 43 | 0 | –CH₂–(4-CF₃-cyclohexyl) | 2-chloro-5-pyridyl | 112° C. |
| 44 | 1 | –CH₂–(4-CF₃-cyclohexyl) | 2-chloro-5-pyridyl | 74–76° C. |

TABLE 1-continued
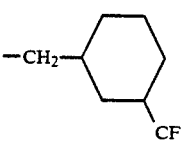
| Ex. No. | n | R | Het | Melting point |
|---|---|---|---|---|
| 45 | 0 | 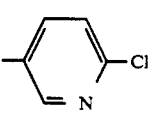 | 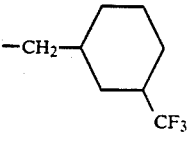 | 129° C. |
| 46 | 1 | 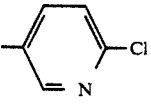 | 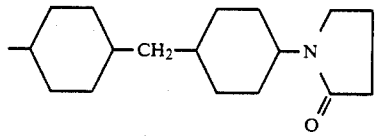 | 126° C. |
| 47 | 1 | 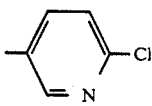 | 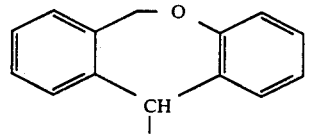 | 130° C. |
| 48 | 1 | 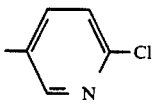 | 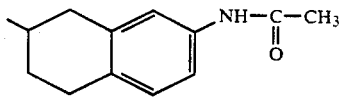 | 185° C. |
| 49 | 0 | 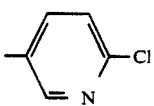 | 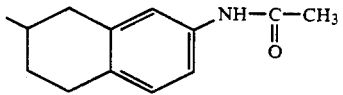 | 212° C. |
| 50 | 1 | 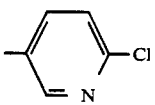 | 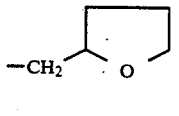 | 165° C. |
| 51 | 0 | 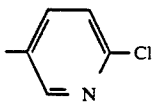 | 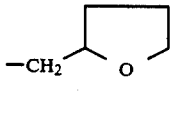 | 138° C. |
| 52 | 1 | 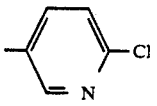 | 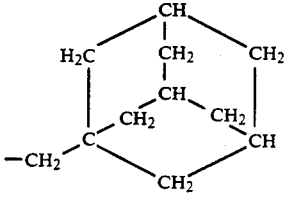 | 101° C. |
| 53 | 0 | 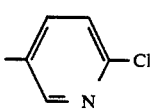 | | 181° C. |

TABLE 1-continued
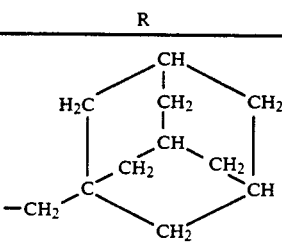
(1)
| Ex. No. | n | R | Het | Melting point |
|---|---|---|---|---|
| 54 | 1 | 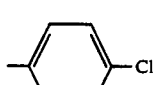 | 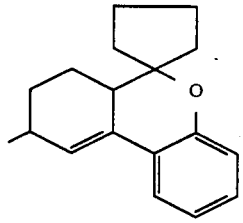 | 178° C. |
| 55 | 1 | 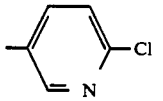 | 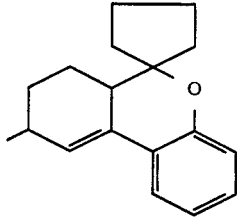 | 155° C. |
| 56 | 1 | 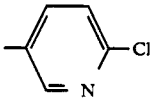 isomer | 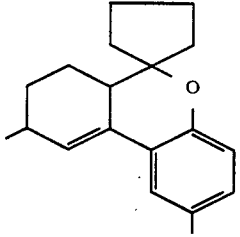 | 158° C. |
| 57 | 1 | 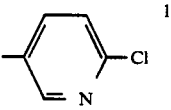 | 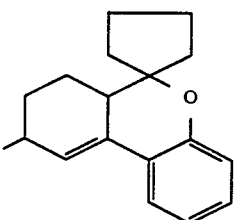 | 140° C. |
| 58 | 1 | 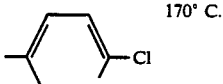 isomer | | 170° C. |

TABLE 1-continued

Structure (I): A six-membered ring with N-R, N, N-CH₂-Het, and the ring bearing =C(NO₂) and connected through (H₂C)ₙ bridge.

| Ex. No. | n | R | Het | Melting point |
|---------|---|---|-----|---------------|
| 59 | 1 | spirocyclopentane-cyclohexene fused with methylchromene (methyl substituent), isomer | 2-chloro-pyridin-5-yl | 115° C. |
| 60 | 1 | 4-methylcyclohexyl-C(=O)-N(C₂H₅)₂ | 2-chloro-pyridin-5-yl | 149° C. |
| 61 | 1 | (CH₃)₂CHCH₂C(CH₃)₂-N(CH₃)-C(CH₃)₂CH₂CH(CH₃)- (bis-tert-alkyl N-methyl amine) | 2-chloro-pyridin-5-yl | 164° C. |
| 62 | 0 | spirocyclopentane-cyclohexene fused with methylchromene | 2-chloro-pyridin-5-yl | 170° C. |
| 63 | 0 | spirocyclopentane-cyclohexene fused with methylchromene, isomer | 2-chloro-pyridin-5-yl | 82° C. |
| 64 | 0 | adamantane-type cage structure with CH₃ substituent | 2-chloro-pyridin-5-yl | 183° C. |

TABLE 1-continued
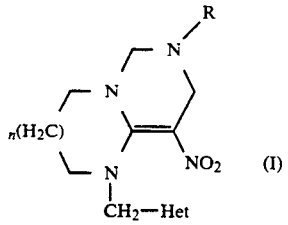
| Ex. No. | n | R | Het | Melting point |
|---|---|---|---|---|
| 65 | 1 | 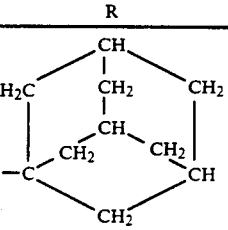 | 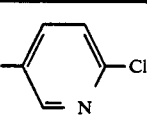 | 164° C. |
| 66 | 0 | 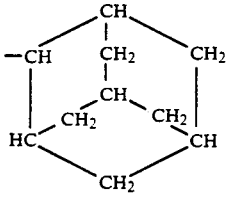 | 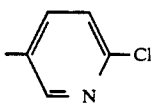 | 164° C. |
| 67 | 1 | 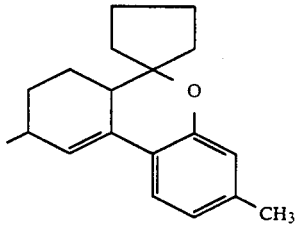 | 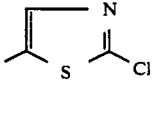 | 130° C. (dec.) |
| 68 | 1 | 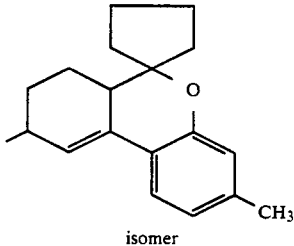 isomer | 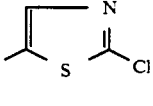 | 174° C. (dec.) |
| 69 | 0 | 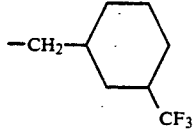 | 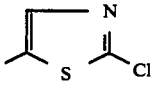 | 125° C. |
| 70 | 0 | 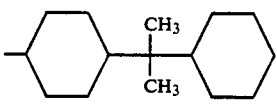 | 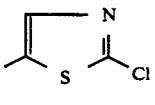 | 155° C. |
| 71 | 0 | 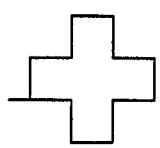 | 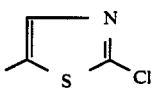 | 167–169° C. |

TABLE 1-continued
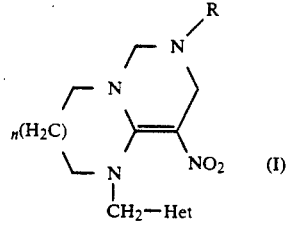
| Ex. No. | n | R | Het | Melting point |
|---|---|---|---|---|
| 72 | 1 | 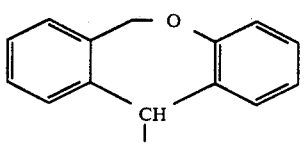 | 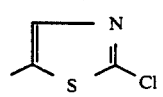 | 203° C. |
| 73 | 1 | 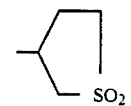 | 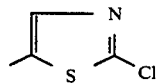 | 3.87;3.91;7.49* |
| 74 | 0 | 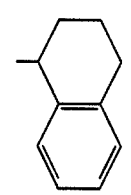 | 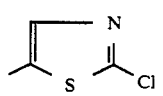 | 103–106° C. |
| 75 | 1 | 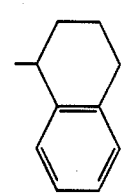 | 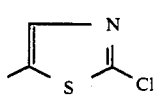 | 169° C. (dec.) |
| 76 | 1 | 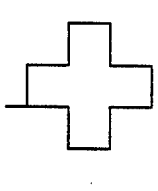 | 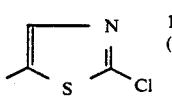 | 185° C. (dec.) |
| 77 | 0 | —CH₂CH₂CH₂—N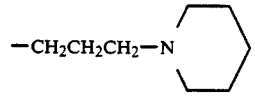 | 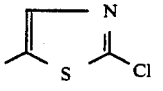 | 119–121° C. |
| 78 | 0 | 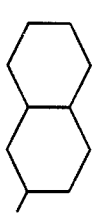 | 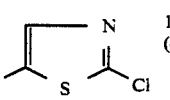 | 148° C. (dec.) |

TABLE 1-continued
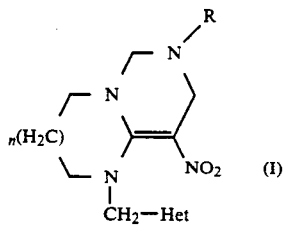 (I)
| Ex. No. | n | R | Het | Melting point |
|---|---|---|---|---|
| 79 | 1 | 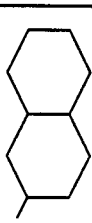 | 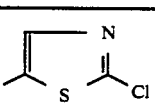 | 133-139° C. |
| 80 | 0 | 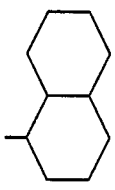 | 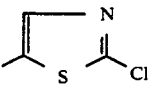 | 148° C. (dec.) |
| 81 | 1 | 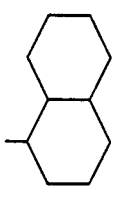 | 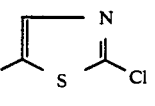 | 150° C. (dec.) |
| 82 | 0 | 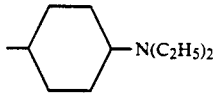 | 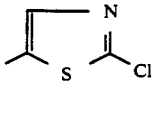 | 122-127° C. |
| 83 | 1 | 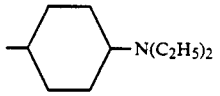 | 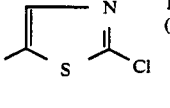 | 157° C. (dec.) |
| 84 | 0 | 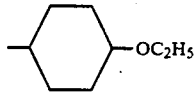 | 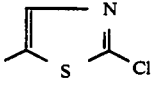 | 83-85° C. |
| 85 | 1 | 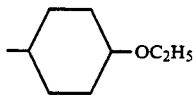 | 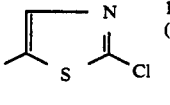 | 127-129° C. (dec.) |
| 86 | 0 | 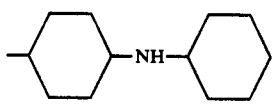 | 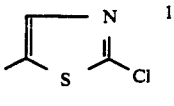 | 136-138° C. |
| 87 | 1 | 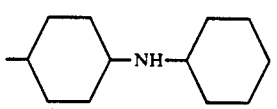 | 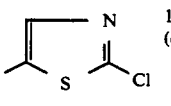 | 161° C. (dec.) |

TABLE 1-continued
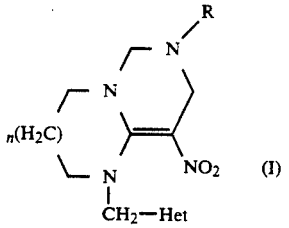
| Ex. No. | n | R | Het | Melting point |
|---|---|---|---|---|
| 88 | 0 | 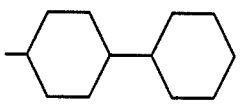 | 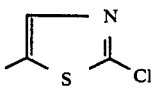 | 210° C. (dec.) |
| 89 | 1 | 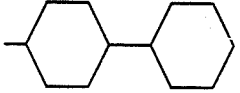 | 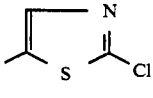 | 180° C. (dec.) |
| 90 | 1 | 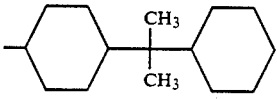 | 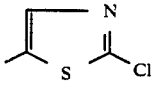 | 155° C. (dec.) |
| 91 | 0 | 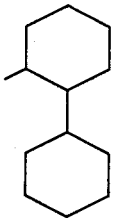 | 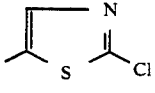 | 74° C. |
| 92 | 0 | 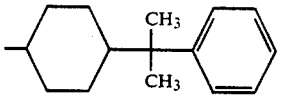 | 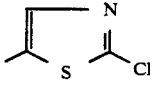 | 170° C. (dec.) |
| 93 | 0 | 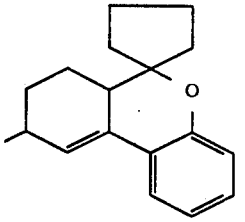 | 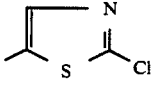 | 105° C. (dec.) |
| 94 | 0 | 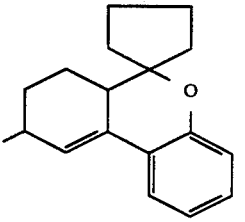 isomer | 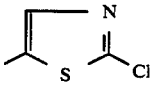 | 107° C. (dec.) |

TABLE 1-continued

Structure (I): Cyclic system with $n(H_2C)$, N-R, N-CH$_2$-Het, =NO$_2$

| Ex. No. | n | R | Het | Melting point |
|---|---|---|---|---|
| 95 | 0 | cyclopentyl-spiro-cyclohexene linked to methylphenol | 2-chloro-5-methylthiazoline | 184° C. (dec.) |
| 96 | 0 | cyclopentyl-spiro-cyclohexene linked to methylphenol (isomer) | 2-chloro-5-methylthiazoline | 117° C. (dec.) |
| 97 | 0 | CH$_2$-spiro-cyclohexene linked to phenol | 2-chloro-5-methylthiazoline | 150° C. (dec.) |
| 98 | 0 | CH$_2$-spiro-cyclohexene linked to phenol (isomer) | 2-chloro-5-methylthiazoline | 178° C. (dec.) |
| 99 | 0 | dibenzosuberyl (CH) | 2-chloro-5-methylthiazoline | 213° C. (dec.) |

TABLE 1-continued

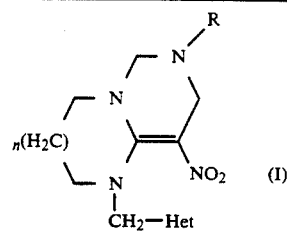

| Ex. No. | n | R | Het | Melting point |
|---|---|---|---|---|
| 100 | 1 | cyclohexyl-cyclohexyl | 2-chloro-5-methylthiazole | 87° C. |
| 101 | 1 | 4-(2-phenylpropan-2-yl)cyclohexyl | 2-chloro-5-methylthiazole | 172° C. (dec.) |
| 102 | 1 | 10,11-dihydro-5H-dibenzo[a,d]cyclohepten-5-yl | 2-chloro-5-methylthiazole | 224° C. |
| 103 | 0 | dibenz[b,f]oxepin-10(11H)-yl | 2-chloro-5-methylthiazole | 151° C. (dec.) |
| 104 | 0 | 4-(N,N-diethylcarbamoyl)cyclohexyl | 2-chloro-5-methylthiazole | 96° C. (dec.) |
| 105 | 0 | —CH₂—(4-CF₃-cyclohexyl) | 2-chloro-5-methylthiazole | 79° C. |
| 106 | 0 | 4-[(4-(2-oxopyrrolidin-1-yl)cyclohexyl)methyl]cyclohexyl | 2-chloro-5-methylthiazole | 151° C. (dec.) |
| 107 | 0 | tetrahydrothiophene-1,1-dioxide-3-ylmethyl | 2-chloro-5-methylthiazole | 196° C. |
| 108 | 1 | 4-(N,N-diethylcarbamoyl)cyclohexyl | 2-chloro-5-methylthiazole | 143° C. (dec.) |

TABLE 1-continued

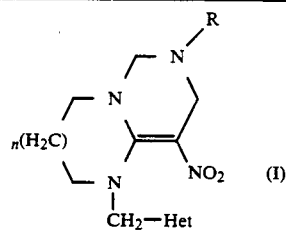

| Ex. No. | n | R | Het | Melting point |
|---|---|---|---|---|
| 109 | 0 | (CH₃)₃C-CH₂-CH(CH₃)-CH₂-C(CH₃)₂-N(CH₃)- (neopentyl-type with N—CH₃) | 5-methyl-thiazol-2-yl-Cl | 167° C. (dec.) |
| 110 | 1 | —CH₂CH₂CH₂—N(piperidyl) | 5-methyl-thiazol-2-yl-Cl | 122–124° C. |
| 111 | 1 | spiro[cyclopentane-chromene] derivative | 5-methyl-thiazol-2-yl-Cl | 124° C. (dec.) |
| 112 | 1 | spiro[cyclopentane-chromene] derivative, isomer | 5-methyl-thiazol-2-yl-Cl | 124–128° C. |
| 113 | 1 | spiro[cyclopentane-chromene]-CH₃ derivative | 5-methyl-thiazol-2-yl-Cl | 120° C. (dec.) |
| 114 | 1 | spiro[cyclopentane-chromene]-CH₃ derivative, isomer | 5-methyl-thiazol-2-yl-Cl | 165° C. (dec.) |

TABLE 1-continued

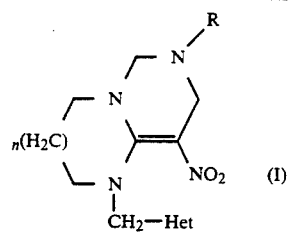

| Ex. No. | n | R | Het | Melting point |
|---|---|---|---|---|
| 115 | 1 | —CH₂—(cyclohexyl)—CF₃ | (chlorothiazole) | 126–129° C. |
| 116 | 1 | (2,2,6,6-tetramethyl-4-methyl-N-methylpiperidinyl group) | (chlorothiazole) | 169° C. (dec.) |
| 117 | 1 | (cyclohexyl-CH₂-cyclohexyl-N-pyrrolidinone) | (chlorothiazole) | 153° C. (dec.) |
| 118 | 0 | (tetrahydronaphthyl-NH-C(O)-CH₃) | (chlorothiazole) | 132° C. |
| 119 | 1 | (tetrahydronaphthyl-NH-C(O)-CH₃) | (chlorothiazole) | 148° C. |
| 120 | 0 | —CH₂—(tetrahydrofuranyl) | (chlorothiazole) | 150° C. |
| 121 | 1 | —CH₂—(tetrahydrofuranyl) | (chlorothiazole) | 161° C. |
| 122 | 0 | —CH₂—C(adamantyl) | (chlorothiazole) | 214° C. |
| 123 | 1 | —CH₂—C(adamantyl) | (chlorothiazole) | 196° C. |

TABLE 1-continued

Structure (I): Piperazine-type macrocycle with R on top N, =NO₂ substituent, and CH₂—Het on bottom N; ring contains n(H₂C) bridge.

| Ex. No. | n | R | Het | Melting point |
|---|---|---|---|---|
| 124 | 0 | (spirocyclopentyl-cyclohexenyl)(2-methylphenyl)methyl ether group with CH₃ | 2-chloro-5-methylenethiazole | 154° C. |
| 125 | 0 | same as 124, isomer | 2-chloro-5-methylenethiazole | 89° C. |
| 126 | 0 | adamantyl-type cage (noradamantyl/tricyclic) | 2-chloro-5-methylenethiazole | 210° C. |
| 127 | 1 | adamantyl-type cage | 2-chloro-5-methylenethiazole | 203° C. |
| 128 | 0 | larger polycyclic cage | 2-chloro-5-methylenethiazole | 208° C. |
| 129 | 1 | larger polycyclic cage | 2-chloro-5-methylenethiazole | 154° C. |

*The ¹H-NMR spectra were recorded in deuterochloroform (CDCl₃) using tetramethylsilane (TMS) as the internal standard. The chemical shift is indicated as the δ value in ppm.

Example A

*Phaedon larvae* test

Solvent: 7 parts by weight of dimethylformamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Cabbage leaves (Brassica oleracea) are treated by being dipped into the preparation of the active compound of the desired concentration and are infested with mustard beetle larvae (Phaedon cochleariae), as long as the leaves are still moist.

After the specified period of time, the destruction in % is determined. 100% means that all the beetle larvae have been killed; 0% means that none of the beetle larvae have been killed.

In this test, for example, the compounds of Preparation Examples 1, 2, 5, 7, 9 to 40, 70, 71, 74, 77, 78, 79 to 89, 90 to 93, 95 to 97, 100, 101, 103, 104, 106, 108, 109, 111 to 114, 116 and 117 showed a degree of destruction of 100% after 3 days at a concentration of active compound of, for example, 0.1%.

Example B

Aphis test (systemic action)

Solvent: 7 parts by weight of dimethylformamide
Emulsifier: 1 part by weight of alkylaryl polyglycol ether To produce a suitable preparation of active compound, 1 part by weight of active compound is mixed with the stated amount of solvent, the stated amount of emulsifier is added, and the concentrate is diluted with water to the desired concentration.

Bean shoots (Vicia faba) which have been heavily infested with the black bean aphid (Aphis fabae) are treated by being dipped into the preparation of the active compound of the desired concentration.

After the specified period of time, the destruction in % is determined. 100% means that all the aphids have been killed; 0% means that none of the aphids have been killed.

In this test, for example, the compounds of Preparation Examples 1, 2, 5, 9 10, 11, 14, 15, 16, 21, 23, 39, 70, 80, 81, 82, 84, 87, 90, 104, 106 and 109 showed a degree of destruction of 100% after 3 days at a concentration of active compound of, for example, 0.1%.

Example C

Test insect: *Phorbia antiqua* grubs in the soil

Solvent: 3 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

The preparation of active compound is intimately mixed with soil. The concentration of the active compound in the preparation is of practically no importance here, only the amount by weight of active compound per unit volume of soil, which is given in ppm (=mg/l), being decisive. The soil is transferred into pots and the pots are left to stand at room temperature.

After 24 hours, the test insects are introduced into the treated soil, and after a further 2 to 7 days the degree of effectiveness of the active compound is determined in % by counting the dead and live test insects. The degree of effectiveness is 100% if all the test insects have been killed and is 0% if just as many test insects are still alive as in the case of the untreated control.

In this test, for example, the compounds of Preparation Examples 5, 71, 77 and 84 showed a degree of destruction of 100% at a concentration of active compound, for example, of 20 ppm.

Example D

Root-systemic action

Test insect: *Myzus persicae*

Solvent: 3 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

The preparation of active compound is intimately mixed with soil. The concentration of the active compound in the preparation is of practically no importance, only the amount by weight of active compound per unit volume of soil, which is given in ppm (=mg/l), being decisive. The treated soil is transferred into pots and these are planted with cabbage (Brassica oleracea). The active compound can in this way be taken up from the soil by the roots of the plants and be transported into the leaves.

To demonstrate the root-systemic effect, exclusively the leaves are infested with the abovementioned test insects after 7 days. After a further 2 days, the evaluation is made by counting or estimating the dead insects. The root-systemic action of the active compound is deduced from the mortality figures. It is 100% if all test insects have been killed and 0% if just as many test insects are still alive as in the case of the untreated control.

In this test, for example, the compounds of Preparation Examples 1, 2, 5, 7, 11, 13, 14, 15, 16, 17, 21, 23, 32, 70, 71, 77, 86, 87, 89, 93, 94, 95, 100, 110 and 111 showed a degree of destruction of 100% at a concentration of active compound, for example, of 20 ppm.

Example E

Root-systemic action

Test insect: *Phaedon cochleariae larvae*

Solvent: 3 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

The preparation of active compound is intimately mixed with soil. The concentration of the active compound in the preparation is of practically no importance, only the amount by weight of active compound per unit volume of soil, which is given in ppm (=mg/l), being decisive. The treated soil is transferred into pots and these are planted with cabbage (Brassica oleracea). The active compound can in this way be taken up from the soil by the roots of the plants and be transported into the leaves.

To demonstrate the root-systemic effect, exclusively the leaves are infested with the abovementioned test insects after 7 days. After a further 2 days, the evaluation is made by counting or estimating the dead insects. The root-systemic action of the active compound is deduced from the mortality figures. It is 100% if all test insects have been killed and 0% if just as many test insects are still alive as in the case of the untreated control.

In this test, for example, the compounds of Preparation Examples 2, 11 and 23 showed a degree of destruction of 100% at a concentration of active compound, for example, of 20 ppm.

Example F

Seed treatment test/soil insects
Test insect: *Phorbia antiqua* grubs in the soil
Test plant: *Albium cepa*
Solvent: 1 part by weight of acetone
Excipient: kaolin To produce a suitable preparation of active compound, the active compound is dissolved in acetone and 1 part by weight of active compound/acetone is mixed with 5 parts by weight of kaolin. The onion seeds are treated with this active compound preparation at the application rates required. They are sown in 0.5 liter pots containing standardized soils at a greenhouse temperature of 20° C.

After emergence of the onions, they are artificially infected with onion fly eggs.

Evaluation is carried out after 14 days. The degree of action is 100% if all the onion plants remain standing, and 0% if all the test plants have been destroyed (as in the untreated control).

In this test, for example, the compound of Preparation Example 7 showed a degree of action of 100% at an amount, for example, of 2 g of active compound/kg of seed.

Example G

Seed treatment test/root-systemic action
Test insect: *Phaedon cochleariae* beetles
Test plant: *Brassica oleracea*
Solvent: 1 part by weight of acetone
Carrier: kaolin To produce a suitable preparation of active compound, the active compound is dissolved in acetone and 1 part by weight of active compound/acetone is mixed with 5 parts by weight of kaolin. The cabbage seeds are treated with this active compound preparation at the application rates required. The cabbage is sown in 0.5 liter pots containing standardized soils at a room temperature of 20° C.

The active compound can thus be taken up from the soil by the plant roots and transported into the leaves.

For detection of the root-systemic effect, exclusively the leaves are infested with the abovementioned test insects after 14 days. After a further 3 days, the evaluation is carried out by counting or estimating the dead insects The root-systemic action of the active compound is derived from the mortality figures. It is 100% if all the test insects have been killed and 0% if just as many test insects are still alive as in the untreated control.

In this test, for example, the compound of Preparation Example 7 showed a degree of action of 100% at an amount, for example, of 2 g of active compound/kg of seed.

Example H

Seed treatment test/root-systemic action
Test insect: *Aphis fabae*
Test plant: *Vicia faba*
Solvent: 1 part by weight of acetone
Carrier: kaolin To produce a suitable preparation of active compound, the active compound is dissolved in acetone and 1 part by weight of active compound/acetone is mixed with 5 parts by weight of kaolin. The cabbage seeds are treated with this active compound preparation at the application rates required. The cabbage is sown in 0.5 liter pots containing standardized soils at a room temperature of 20° C.

The active compound can thus be taken up from the soil by the plant roots and transported into the leaves.

For detection of the root-systemic effect, exclusively the leaves are infested with the abovementioned test insects after 14 days. After a further 3 days, the evaluation is carried out by counting or estimating the dead insects The root-systemic action of the active compound is derived from the mortality figures. It is 100% if all the test insects have been killed and 0% if just as many test insects are still alive as in the untreated control.

In this test, for example, the compound of Preparation Example 5 showed a degree of action of 100% at an amount, for example, of 2 g of active compound/kg of seed.

Example I

Test with Lucilia cuprina resistant larvae
Solvent: 35 parts by weight of ethylene glycol monomethyl ether 35 parts by weight of nonylphenol polyglycol ether To produce a suitable preparation of active compound, three parts by weight of active compound are mixed with seven parts by weight of the abovementioned solvent mixture and the concentrate thus obtained is diluted with water to the particular desired concentration.

About 20 Lucilia cuprina res. larvae are introduced into a test tube which contains approx. 1 cm$^3$ of horse meat and 0.5 ml of the preparation of active compound. After 24 hours, the degree of destruction is determined.

In this test, for example, the compounds of Preparation Examples 1, 2, 5, 6, 7, 9, 10 to 35, 37, 39, 70, 71, 74 to 104, 106, 108, 109, 111 to 114, 116 and 117 showed a degree of destruction of 100% at a concentration of active compound, for example, of 100 ppm.

Example K

Test with Blattella germanica
Filter paper discs ($\phi$9 cm from Schleicher & Schüll BF) are each impregnated in plastic dishes with 2.0 ml of the desired concentration of the test substance in each case.

After drying the filter, the dishes are closed and 5 Blatella germanica anaesthetized with $CO_2$ are in each case added 24 hours after the start.

Dosages: 1000, 100, 10 ppm.

The action is recorded at specified times after adding the Blattella germanica (5–360 minutes and 1–7 days p.a. after adding the Blattella germanica).

The attainment of the so-called adynamic stage (no life signs) of the test arthropods serves as a criterion of the onset of action.

100% action means that all Blattella germanica have been killed, 0% action means that none of the Blattella germanica have been killed.

In this test, for example, the compounds of Preparation Examples 9, 11, 19, 23, 78, 80, 81, 89, 93, 94, 95, 96, 98, 112 and 113 showed a destruction of 100% at a concentration, for example, of 1000 ppm.

Example L

Test with Sitophilus granarius

Filter paper discs ($\phi$9 cm from Schleicher & Schüll BF) are each impregnated in plastic dishes with 2.0 ml of the desired concentration of the test substance in each case.

After drying the filter, the dishes are closed and 10 Sitophilus granarius anaesthetized with $CO_2$ are in each case added 24 hours after the start.

The action is recorded at specified times after adding the Sitophilus granarius (5-360 minutes and 1-7 days p.a. after adding the Sitophilus granarius).

The attainment of the so-called adynamic stage (no life signs) of the test arthropods serves as a criterion of the onset of action.

100% action means that all Sitophilus granarius have been killed, 0% action means that none of the Sitophilus granarius have been killed.

In this test, for example, the compounds of Preparation Examples 1, 10 to 21, 23 to 30, 32, 34, 35, 37, 70, 78 to 101, 103, 104, 108, 109, 111 to 114, 116 and 117 showed a destruction of 100% at a concentration, for example, of 1000 ppm.

It is understood that the specification and examples are illustrative but not limitative of the present invention and that other embodiments within the spirit and scope of the invention will suggest themselves to those skilled in the art.

We claim:

1. A 1,2,3,4-tetrahydro-5-nitropyrimidine derivative of the formula

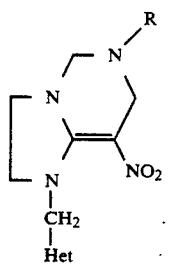

(I)

in which

Het represents pyridyl optionally substituted by halogen and

R unsubstituted cycloalkyl having 9 to 16 carbon atoms; cycloalkyl having 7 to 16 carbon atoms, to which 1 or 2,6-membered aromatic or saturated carbocycles are fused, monosubstituted to trisubstituted cyclohexyl which is substituted by alkoxy having 1 to 4 carbon atoms, mono- or dialkylamino in each case having 1 to 4 carbon atoms in the individual alkyl moieties, cycloalkylamino having 3 to 7 carbon atoms, mono- or dialkylaminocarbonyl in each case having 1 to 4 carbon atoms in the individual alkyl moieties, cycloalkyl having 3 to 7 carbon atoms, cycloalkylalkyl having 3 to 7 carbon atoms in the cycloalkyl and 1 to 5 carbon atoms in the alkyl moiety or by phenylalkyl having 1 to 4 carbon atoms in the alkyl moiety, cyclohexyl, to which 1 or 2 6-membered aromatic or saturated carbocycles are fused, cycloalkylalkyl having 3 to 7 carbon atoms in the cycloalkyl and 1 to 4 carbon atoms in the alkyl moiety, which is monosubstituted to trisubstituted in the cycloalkyl moiety by alkyl or halogenoalkyl in each case having 1 to 4 carbon atoms and optionally 1 to 9 fluorine or chlorine atoms, or one of the following groupings which are optionally substituted by alkyl having 1 to 4 carbon atoms:

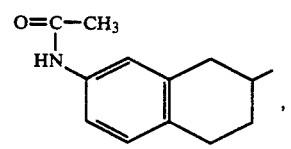

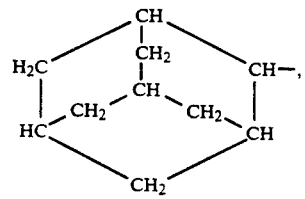

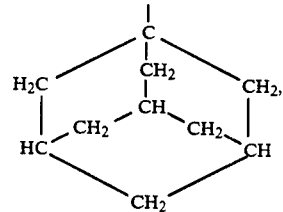

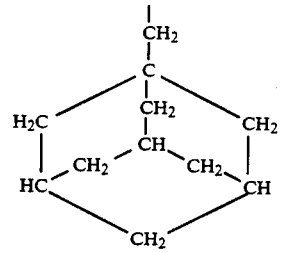

or an agriculturally acceptable acid addition salt thereof.

2. A compound or an agriculturally acceptable salt thereof according to claim 1, in which unsubstituted cycloalkyl having 9 to 12 carbon atoms; cycloalkyl having 7 to 12 carbon atoms, to which 1 or 2 6-membered aromatic carbocycles are fused; monosubstituted or disubstituted cyclohexyl, which is substituted by methoxy, ethoxy, n- or i-propoxy, methylamino, dimethylamino, ethylamino, diethylamino, ethylmethylamino, n-propylamino, di-(n-propyl)amino, methyl(n-propyl)amino, ethyl(n-propyl)amino, isopropylamino, di(isopropyl)amino, methylisopropylamino,ethylisopropylamino, isopropyl(n-propyl)amino or cyclopentylamino, cyclohexylamino, methylaminocarbonyl, dimethylaminocarbonyl,ethylaminocarbon-yl, diethylaminocarbonyl, ethylmethylaminocarbonyl, n- propylaminocarbonyl, di(n-propyl)aminocarbonyl, methyl(n-propyl)aminocarbonyl, ethyl(n-propyl)aminocarbonyl, isopropylaminocarbonyl, di(isopropyl)-aminocarbonyl, methylisopropylaminocarbonyl, ethylisopropylaminocarbonyl, isopropyl(n-propyl)aminocarbonyl, cyclopentyl, cyclohexyl, cyclopentylmethyl, cyclopentylethyl, cyclopentyl-n-propyl, cyclopentylisopropyl, cyclohexylmethyl, cyclohexylethyl, cyclohexyl-n-propyl, cyclohexylisopropyl, phenylmethyl, phenylethyl, phenyl-n-propyl or phenylisopropyl, cyclohexyl to which 1 or 2 6-membered aromatic or saturated carbocycles are fused, cyclopentylmethyl, cyclopentylethyl, cyclohexylmethyl or cyclohexylethyl, these radicals being monosubstituted or disubstituted in the cycloalkyl moiety by methyl or trifluoromethyl, or one of the following groupings:

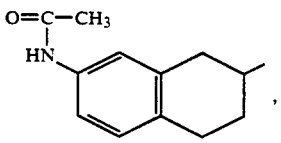

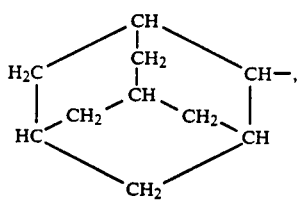

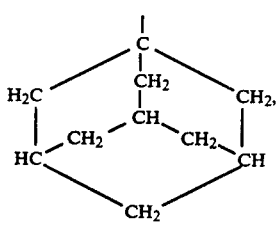

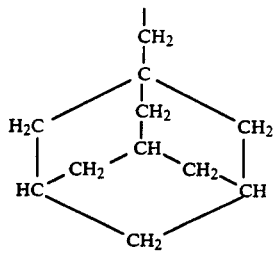

3. An insecticidal composition comprising an insecticidally effective amount of a compound or an agriculturally acceptable salt thereof according to claim 1 and a diluent.

4. A method of combating insects which comprises applying to such insects or to an insect habitat an insecticidally effective amount of a compound or an agriculturally acceptable salt thereof according to claim 1.

5. A compound or an agriculturally acceptable salt thereof according to claim 1, in which
R represents

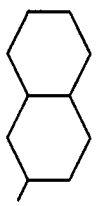

and
Het represents

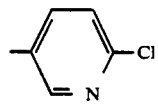

6. A compound or an agriculturally acceptable salt thereof according to claim 1, in which
R represents

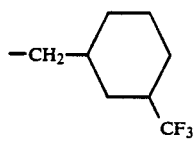

and
Het represents

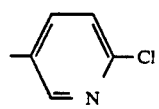

* * * * *

UNITED STATES PATENT AND TRADEMARK OFFICE
CERTIFICATE OF CORRECTION

PATENT NO. : 5,223,502
DATED : June 29, 1993
INVENTOR(S) : Gesing, et al.

It is certified that error appears in the above-identified patent and that said Letters Patent is hereby corrected as shown below:

Col. 54, line 54     After " which " insert -- Het represents

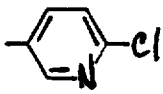

R --

Col. 54, line 67     Delete " ethylaminocarbon-yl " and substitute -- ethylaminocarbonyl --

Signed and Sealed this

Twenty-first Day of March, 1995

Attest:

BRUCE LEHMAN

*Attesting Officer*     *Commissioner of Patents and Trademarks*